US011109885B2

(12) United States Patent
Alvarez

(10) Patent No.: US 11,109,885 B2
(45) Date of Patent: Sep. 7, 2021

(54) BUTTONHOLE TOOL

(71) Applicant: Heather Lee Alvarez, Sutter, CA (US)

(72) Inventor: Heather Lee Alvarez, Sutter, CA (US)

( * ) Notice: Subject to any disclaimer, the term of this patent is extended or adjusted under 35 U.S.C. 154(b) by 74 days.

(21) Appl. No.: 16/186,080

(22) Filed: Nov. 9, 2018

(65) Prior Publication Data

US 2019/0076165 A1 Mar. 14, 2019

Related U.S. Application Data

(63) Continuation of application No. 14/306,930, filed on Jun. 17, 2014, now Pat. No. 10,123,818.

(60) Provisional application No. 61/964,712, filed on Jan. 13, 2014.

(51) Int. Cl.
*A61B 17/3209* (2006.01)
*A61M 5/32* (2006.01)
*A61M 39/02* (2006.01)
*A61M 1/36* (2006.01)

(52) U.S. Cl.
CPC ..... *A61B 17/32093* (2013.01); *A61M 1/3655* (2013.01); *A61M 5/3286* (2013.01); *A61M 39/0247* (2013.01)

(58) Field of Classification Search
CPC .......... A61B 17/32093; A61M 5/3286; A61M 1/3655; A61M 39/0247
See application file for complete search history.

(56) References Cited

U.S. PATENT DOCUMENTS

| 145,217 | A | * | 12/1873 | Leiter |
| 2,697,438 | A | | 12/1954 | Hickey |
| 3,533,411 | A | | 10/1970 | McKnight |
| 3,538,915 | A | | 11/1970 | Frampton |
| 3,624,747 | A | | 11/1971 | McKnight |
| 3,640,275 | A | | 2/1972 | Burke |
| D257,885 | S | | 1/1981 | Kulle |
| 4,641,662 | A | | 2/1987 | Jaicks |
| 5,586,989 | A | | 12/1996 | Bray |
| 5,846,250 | A | | 12/1998 | Parker |
| 6,783,976 | B2 | | 8/2004 | Peterson |
| 6,793,662 | B1 | | 9/2004 | Watermeier |
| D634,425 | S | | 3/2011 | Watanabe |
| 8,328,772 | B2 | * | 12/2012 | Kinast ................. A61M 5/3286 604/274 |
| 8,506,536 | B2 | | 8/2013 | Schnell |

* cited by examiner

*Primary Examiner* — Julian W Woo
(74) *Attorney, Agent, or Firm* — Fish & Richardson P.C.

(57) ABSTRACT

Some implementations provide a tool that includes a gripping portion that includes a first substantially flat surface and a second substantially flat surface arranged substantially parallel to the first surface and coupled to the first surface by at least one side surface, wherein the gripping portion is shaped and sized such that a user can hold the gripping portion between a thumb and forefinger of the user; and a prying portion that includes a first end portion, a second end portion, and a shaft portion connecting the first end portion and the second end portion, wherein the first end portion is shaped and sized for the user holding the gripping portion to pry scab tissue away from a patient's skin and the second end portion is coupled to the gripping portion at the at least one side surface.

12 Claims, 7 Drawing Sheets

BUTTONHOLE TOOL

CROSS-REFERENCE TO RELATED APPLICATIONS

This application is a continuation of U.S. application Ser. No. 14/306,930, filed Jun. 17, 2014, now U.S. Pat. No. 10,123,818, issued Nov. 13, 2018, which claims benefit of U.S. provisional Patent Application 61/964,712, filed Jan. 13, 2014, the contents of which are hereby incorporated by reference in their entirety.

TECHNICAL FIELD

This application relates generally to a tool to assist in creating a buttonhole site for a fistula.

BACKGROUND

Vascular access may be required in a variety of procedures such as dialysis treatment for patients with kidney diseases.

SUMMARY

In one aspect, some implementations provide a tool comprising: a gripping portion comprising a first substantially flat surface and a second substantially flat surface arranged substantially parallel to the first surface and coupled to the first surface by at least one side surface, wherein the gripping portion is shaped and sized such that a user can hold the gripping portion between a thumb and forefinger of the user; and a prying portion comprising a first end portion, a second end portion, and a shaft portion connecting the first end portion and the second end portion, wherein the first end portion is shaped and sized for the user holding the gripping portion to pry scab tissue away from a patient's skin and the second end portion is coupled to the gripping portion at the at least one side surface.

Implementations may include one or more of the following features. The first end portion of the prying portion may include a scoop bevel configured to pry scab tissue from a patient's skin. The gripping portion and the prying portion may be integrally formed. The second end portion is integrally coupled to the gripping portion at the at least one side surface. The second end portion is removably coupled to the gripping portion at the at least one side surface.

A length of the prying portion from the first end portion to the second end portion is between 1 cm to 8 cm. The first surface and the second surface are generally rectangular and the at least one side surface includes at least four side surfaces connecting the first surface to the second surface. The first surface and the second surface are generally square. The first surface and second surface include rounded corners. The first surface may include an indentation located substantially in the center of the first surface. The indentation may be a circular indentation. The tool may be packaged in a sterile package.

In another aspect, some implementations may provide a method for creating a buttonhole site using a tool that includes a gripping portion and a prying portion, the method including: holding the gripping portion between a thumb and forefinger, the gripping portion comprising a first substantially flat surface and a second substantially flat surface arranged substantially parallel to the first surface and coupled to the first surface by at least one side surface; moving the tool such that a first end portion of the prying portion is in contact with scab tissue on a patient's skin, the prying portion comprising the first end portion, a second end portion, and a shaft portion connecting the first end portion and the second end portion, wherein the second end portion is coupled to the gripping portion at the at least one side surface and the first end portion is shaped and sized to pry scab tissue away from a patient's skin; prying the scab tissue away from the patient's skin using the first portion of the prying portion in contact with the scab tissue; and forming a tunnel through the patient's skin where the scab tissue was located.

The first surface includes an indentation located substantially in the center of the first surface and holding the gripping portion between a thumb and forefinger may include placing a ball of the thumb in the indentation and placing the forefinger in contact with the second surface. The first end portion of the prying portion may include a scoop bevel and moving the tool such that a first end portion of the prying portion is in contact with scab tissue on a patient's skin comprises moving the tool such that the scoop bevel is in contact with an edge of the scab tissue. Prying the scab tissue may include applying a torque to the gripping portion using the thumb and forefinger such that the scoop bevel lifts the scab tissue away for the patient's skin.

Forming the tunnel may include inserting a needle through the patient's skin and into a blood vessel. The blood vessel may be part of a fistula. The blood vessel may be an artery. The blood vessel may be a vein.

The details of one or more implementations are set forth in the accompanying drawings and the description below. Other features, objects, and advantages will be apparent from the description and drawings, and from the claims.

DETAILED DESCRIPTION

Figure 1A:
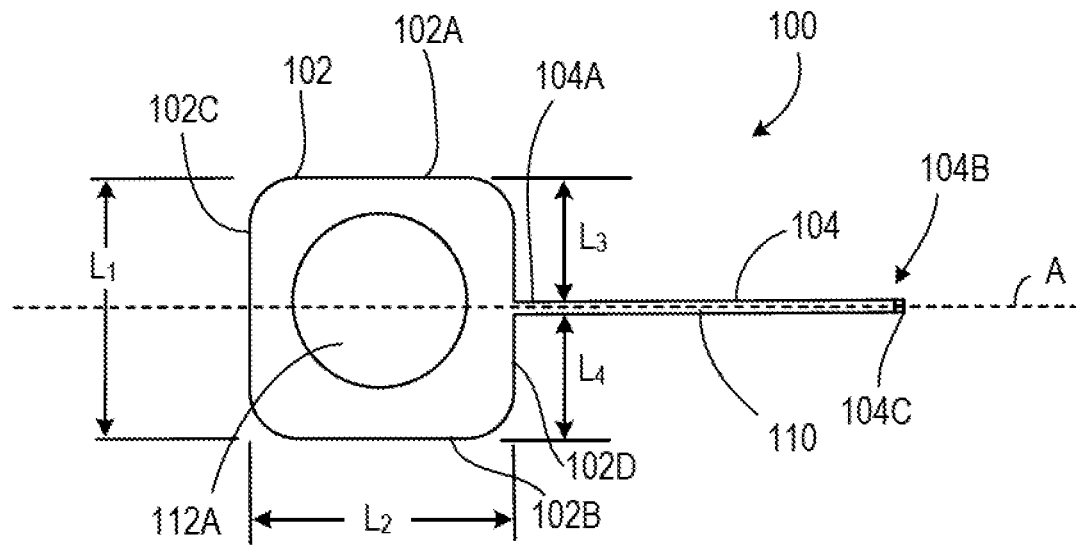
FIG. 1A shows a top view of an example of a buttonhole tool.

Vascular access has become a pre-requisite in a number of therapeutic treatments, including, for example, dialysis. Such therapeutic treatments generally include routine infusion through a vascular access port from, for example, the venous side or the arterial side. The vascular access port may provide an opening on the skin to accommodate the insertion of a needle device into a blood vessel under the skin. The needle device generally connects to a tubing that in turn is linked to, for example, a reservoir of fluid for infusion. The provision of the opening is generally included in a cannulation protocol. The buttonhole tool, as disclosed herein, can facilitate cannulation by simplifying the otherwise laborious process of removing a scab tissue from the surrounding skin to expose the vascular access port.

By way of example, a fistula is typically created in a patient receiving dialysis for treating kidney disease. The fistula provides vascular access so that the patient's blood can be passed through a dialysis machine. To that end, one or more vascular access ports are formed for accessing the arterial or venous aspects of the fistula. One technique for forming the vascular access is referred to as the buttonhole technique. In this technique, a sharp needle is inserted into the same location for each treatment until scar tissue forms a (relatively) permanent tunnel through the skin (similar to an ear piercing). After this tunnel is formed, a blunt needle can be used to access the fistula.

Particularly when first forming the tunnel, scab tissue often develops on the top of the patient's skin at the location of the vascular access port. Because the needle needs to be inserted at the same location for each treatment, the scab needs to be removed for each treatment. The disclosed buttonhole tool can be used to pry off the scab tissue. Some implementations may allow the user to do so safely with little discomfort to the patient and without undue stress on the user.

For context, compared to other approaches for removing a scab tissue for vascular access port, the fistula approach is less prone to infection or complication. The fistula also tends to last longer for repeated vascular access. As a result, the fistula approach is favored by nephrologists, hemo dialysis technicians, and patients. Under this approach, a technician may use a sharp needle on a fistula to create a cannula to access blood vessels for dialysis. The same spot may be used until a piercing like hole is created. This hole with a scab on top is known as a buttonhole needle site. The buttonhole needle site may be created for dialysis patients to receive dialysis treatment more conveniently. In some instances, the buttonhole technique may lead to less pain resulting from the needle stick. In other instances, the buttonhole technique may prevent aneurysms and help keep the fistula healthy for the patient.

Referring to FIGS. 1A-1F, an example of a buttonhole tool 100 includes a gripping portion 102 and a prying portion 104. The gripping portion 102 is shaped and sized such that a user can hold the gripping portion between a thumb and forefinger of the user, and the prying portion is designed to remove a scab from the skin of a patient.

The gripping portion 102 includes front surface 103A and back surface 103B. The front surface 103A and back surface 103B are substantially square in shape and are coupled to each other by side surfaces 102A, 102B, 102C, and 102D. The corners of the front surface 103A and back surface 103B are rounded, which may prevent injury to the user or patient or damage to any packaging or other items.

Figure 1B:
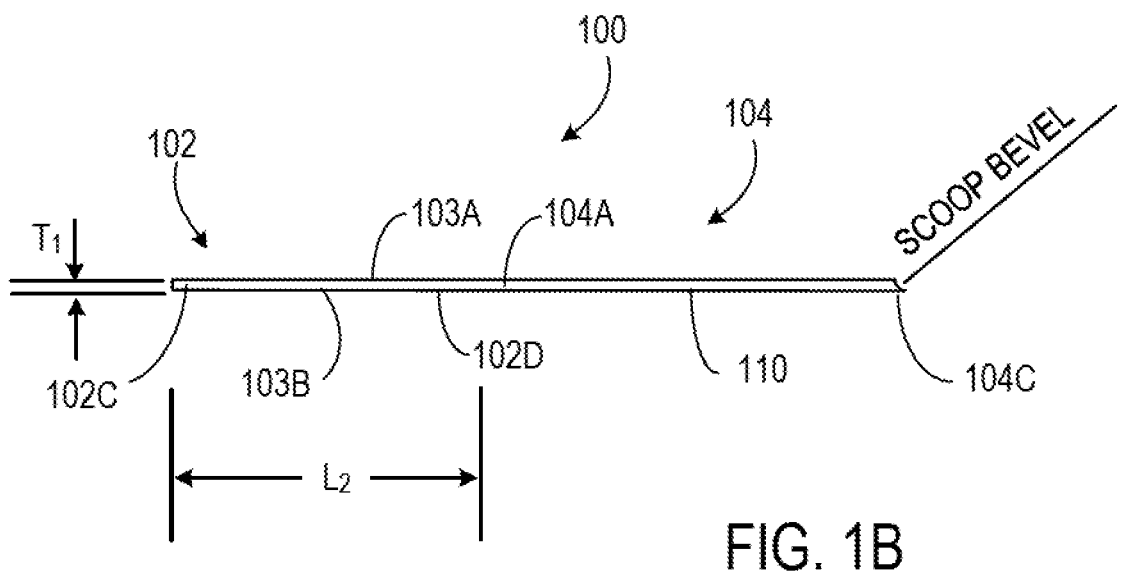
FIG. 1B shows a side view of the buttonhole tool.
Figure 1C:
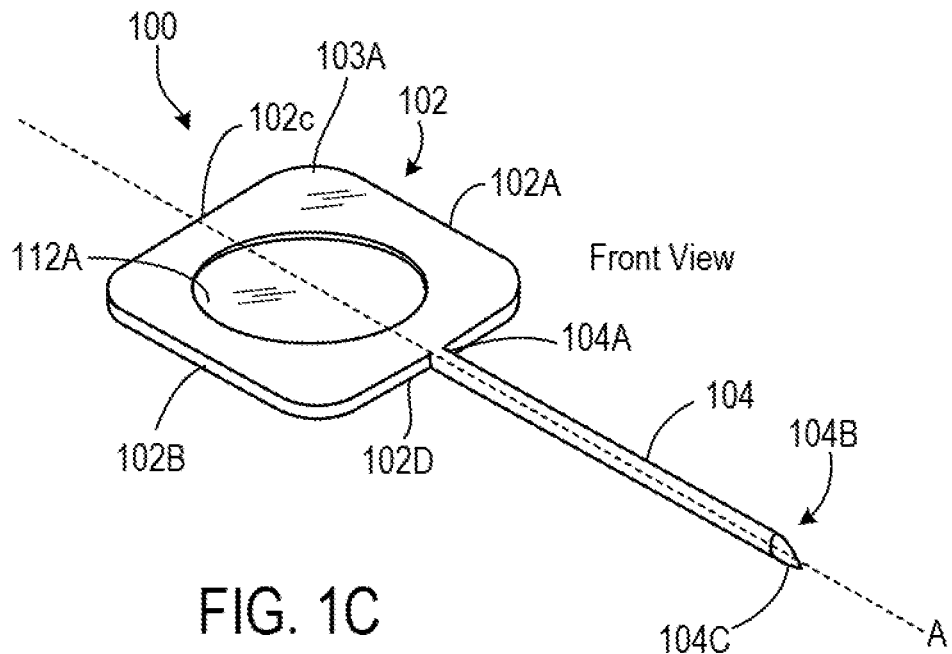
FIGS. 1C and 1D show perspective views of the buttonhole tool.

Particularly referring to FIGS. 1A and 1C, the front surface 103A is substantially flat without any major depressions or plateaus except for an indentation area 112A that is located in substantially the center of the front surface 103A. In particular, the indentation area 112A is a circular depression in the front surface 103A that has a central, normal axis that is aligned with a central, normal axis of the front surface 103A. Indentation area 112A may be depressed, for example, about 0.1 in below the level of the flat surface of front surface 103A. The indentation area 112A is sized so that a user's thumb may fit into the indentation area 112A. The indentation area 112A provides an that can help prevent the thumb or other finger of the user from slipping off front surface 102. Other implementations may use other patterns, either additionally or as an alternative to the indentation area 112A, to help prevent a finger from slipping when the tool is in operation. For example, cross-hatching may be provided on the front surface 103A to help prevent slipping. In some implementations, the indented area 112A may also provide an ornament or an identity mark for the manufacturer, the designer, the user, or the managing clinic.

Figure 1D:
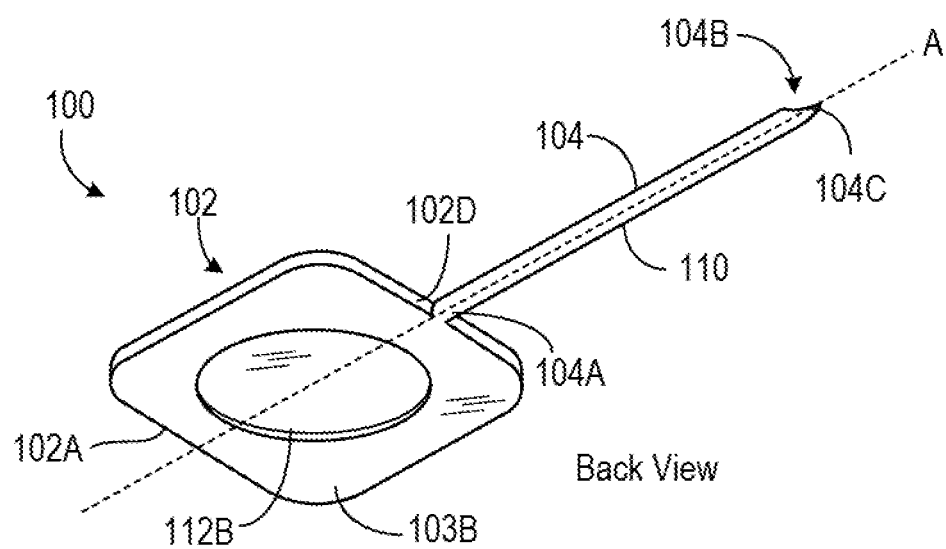

As noted above, gripping portion 102 also includes back surface 103B, as particularly shown in FIGS. 1B and 1D. Back surface 103B includes a flat surface and is substantially parallel with front surface 103A. The flat surface is shaped for contact with an user's forefinger, such as the index finger. Back surface 103B may be separated from front surface 103A by a thickness T1, as illustrated in FIG. 1B. T1 may be, for example, less than 0.6 in.

As illustrated, the back surface 103B may also include an indentation area 112B with a circular contour. A portion of the user's forefinger may fit into the indentation area 112B and, similar to indentation area 112A, indentation area 112B may help prevent slipping of the user's forefinger. Other patterns may be used in addition or as an alternative to help prevent the finger from slipping while the tool is in operation. In some implementations, the indented area may also provide an ornament or an identity mark for the manufacturer, the designer, the user, or the managing clinic. In some configurations, back surface 103B may not include the indentation area 112B or other pattern and, instead, may be a relatively smooth, flat surface.

Front surface 103A and back surface 103B may include sufficient areas to accommodate the palm side of a fore finger or a thumb of the human user. Compared to a simple stem, the surface areas may give an user more ability to control the movement of prying portion 104 to safely remove the scab and expose the buttonhole.

Referring to FIG. 1A, as noted above, gripping portion 102 is surrounded by four side surfaces, namely 102A, 102B, 102C, and 102D that couple the front surface 112A to back surface 103B. As illustrated, side surface 102C has a length, L1, and side surfaces 102A and 102B have a length, L2 in width. In some instances, L1 and L2 are in the range from about 0.5 to 1.2 in, commensurate with thumb size or forefinger size of a user. Different values of L1 and L2 can be used to manufacture in the tool 100 in various sizes including, for example, large, medium, and small, to account for size variations of the users. In the configuration shown, where the front surface 103A is square, side surfaces 102A-102D are substantially the same in length. In this configuration, L1 is similar or identical to L2 in length. In other configurations, such as where the front surface 103A is rectangular, L1 and L2 are different.

Side surface 102D includes an upper length L3 and a lower length L4. These two dimensions indicate the distances from prying portion 104 to side surface 102A and from prying portion 104 to side surface 102B, respectively. In the configuration shown, the prying portion 104 is coupled to the gripping portion 102 at side surface 102D at a position that is located substantially along the midline axis A of too 100, as shown in FIG. 1A. In this configuration, L3 is substantially identical to L4, or about half the dimension of L1 or L2. Moreover, the difference between L1 and the sum of L3 and L4 correspond to the thickness of prying portion 104.

Referring to FIG. 1A, prying portion 104 includes a first end portion 104B, second end portion 104A, and shaft 110 connecting the first end portion 104B and second end portion 104A. The shaft 110 may be approximately 0.5 in to 3 in (e.g., about 1 cm to 8 cm) long. The second end portion 104A couples the prying portion 104 to gripping portion 102 at side surface 102D. The coupling may be permanent, thereby integrating the prying portion 104 with the gripping portion 102. The integral coupling may provide a robust connection between the gripping portion 102 and the prying portion 104 to reduce the chances of prying portion 104 snapping off the gripping portion 102 during operation. As an example, the gripping portion 102 and prying portion 104 may be formed as a single piece of material, such as plastic.

In other cases, however, the coupling may provide a removable attachment of the prying portion 104 to gripping portion 102. In one instance, the second end portion 104A may mate with gripping portion 102, for example, through a threading mechanism. The removable attachment may enable prying portions with shafts of varying length to be mounted on the gripping portion 104.

Figure 1E:
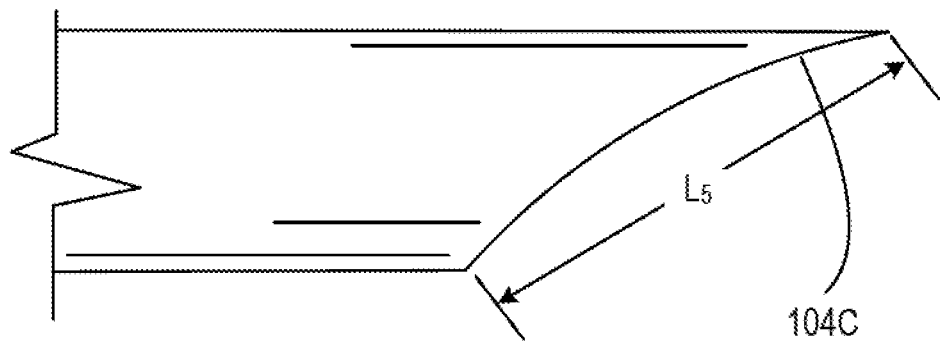
FIGS. 1E and 1F show the scoop bevel the buttonhole tool.
Figure 1F:
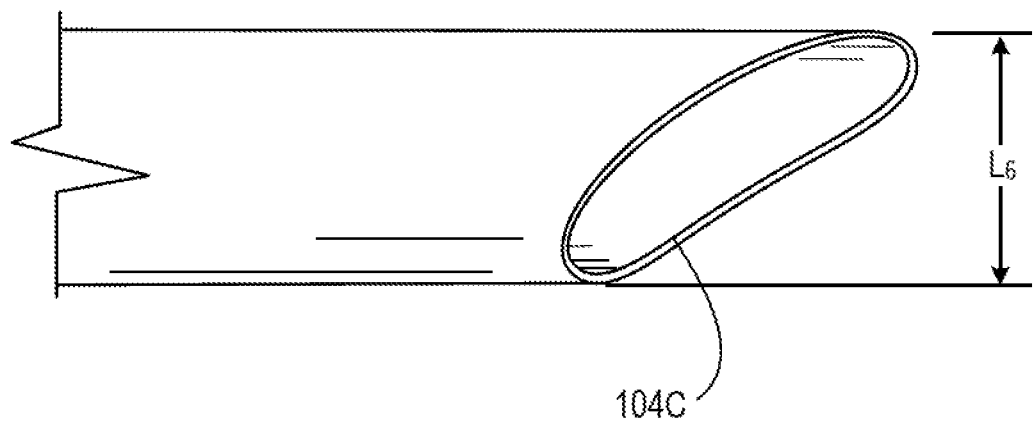

The first end portion 104B is shaped and sized to pry scab tissue away from a patient's skin. To that end, for example, the first end portion 104B may include a scoop bevel 104C. Referring particular to FIGS. 1E and 1F, scoop bevel 104C has a concave profile. The concave profile, in combination with a pointed edge at the tip, may be particularly suited for prying scab tissue from underneath. In that case, scoop bevel 104C can operate as a shovel head in removing scab tissue. The user may use the pointed tip to get underneath scab tissue and then use the concave profile to extend the contact area underneath the scab tissue, leading to easier and more efficient removal of scab tissue. As illustrated in FIG. 1E, the concave profile of scoop bevel 104C is L5 in length.

Particularly referring to FIG. 1F, scoop bevel 104C has an extended and enlarged surface area, similar to that of a spoon, well suited to contain and lift a potentially large volume of scab tissue chuck. As illustrated in FIG. 1F, the spoon shape of scoop bevel 104C measures L6 in width. In some example configurations, the scoop bevel may be approximately 0.2-0.4 in length and 0.1-0.3 in width, commensurate with the dimension range of typical scab tissues. The concave portion may have a radius of approximately 2 in.

Buttonhole tool 100 can be made of a solid piece of plastic, wood, or even light metal. Buttonhole tool 100 may be individually packaged and maintained as a sterile package for one-time use. In other words, buttonhole tool 100 may be a disposable device. In one instance, shaft 110 with a scoop bevel end may be covered to prevent injury and discarded in sharps container after disposal.

For certain dialysis techniques, such as the buttonhole technique, scab tissue needs to be removed each time at the arterial and the venous buttonhole sites. The buttonhole tool 100 can enable a user to safely remove the scab. The gripping portion 102 is shaped and sized such that a user can hold the gripping portion 102 between a thumb and a forefinger, while the prying portion 104 is shaped and sized to pry scab tissue away from a patient's skin. To that end, prying portion 104 includes scoop bevel 104C at the end of the shaft 110 to allow the user (e.g., a dialysis technician) to get under the scab for fast removal. For example, the user may grasp the gripping portion 102 between their thumb and forefinger, and initially pry under a scab tissue to make contact with the skin of the patient at scoop bevel 104C. Relying on a prying motion, the user may generate a torque through the contact point by applying a force at gripping portion 102. The torque can be leveraged over shaft 110 to break off scab tissue. Thus, the user may no longer need to hunch over the patient. As such, the tool may reduce back strain on dialysis technicians.

Figure 2A:
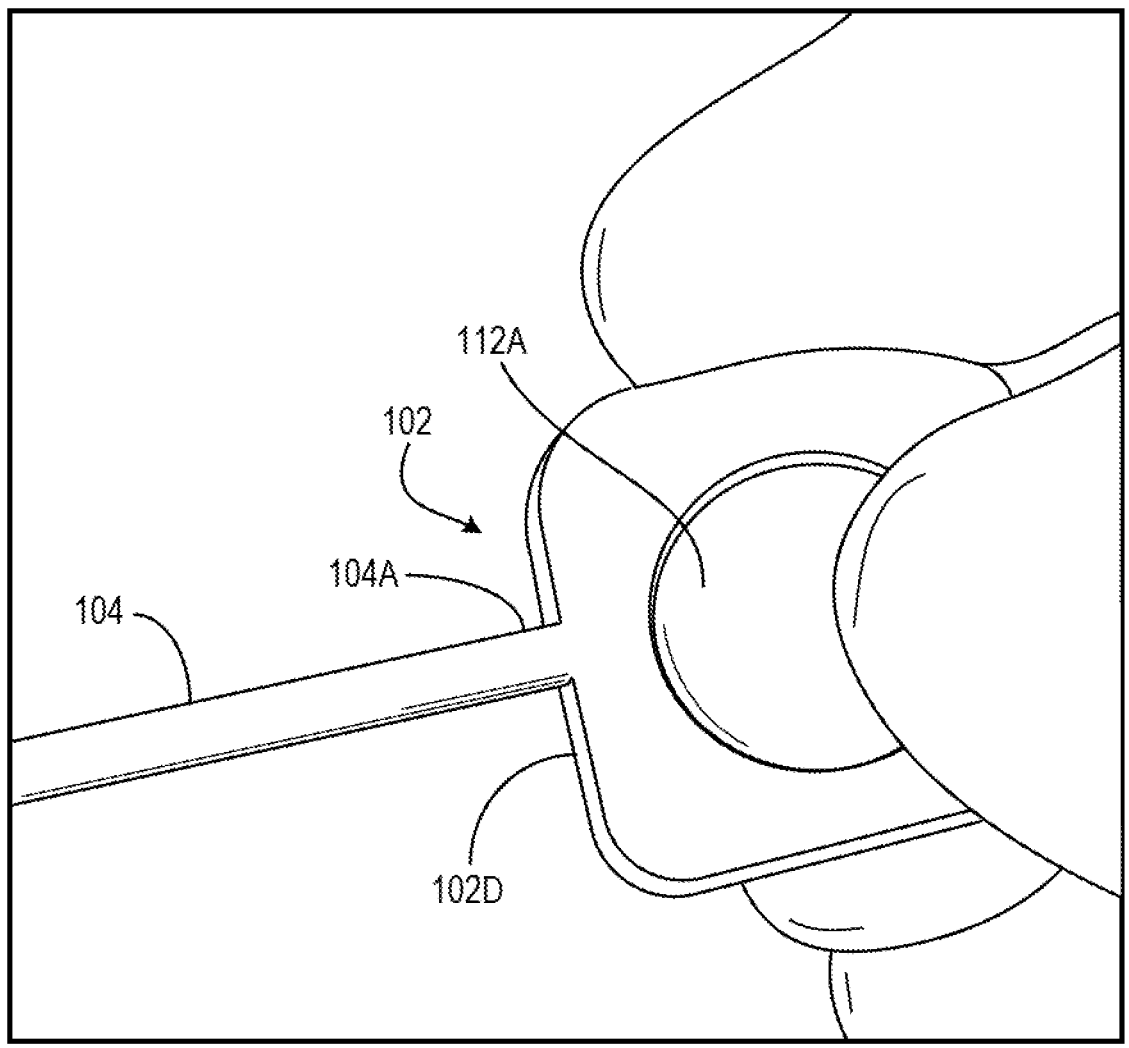
FIG. 2A is an illustration showing a user holding the buttonhole tool.

FIG. 2A is shows a user holding the buttonhole tool 100. The user is holding the tool using the gripping portion 102. Holding gripping portion 102, the user may take buttonhole tool 100 from a package and inspect buttonhole tool 100 for integrity. If the inspection of the tool identifies no defects, the user may then aim the tool at a target scab tissue.

Figure 2B:
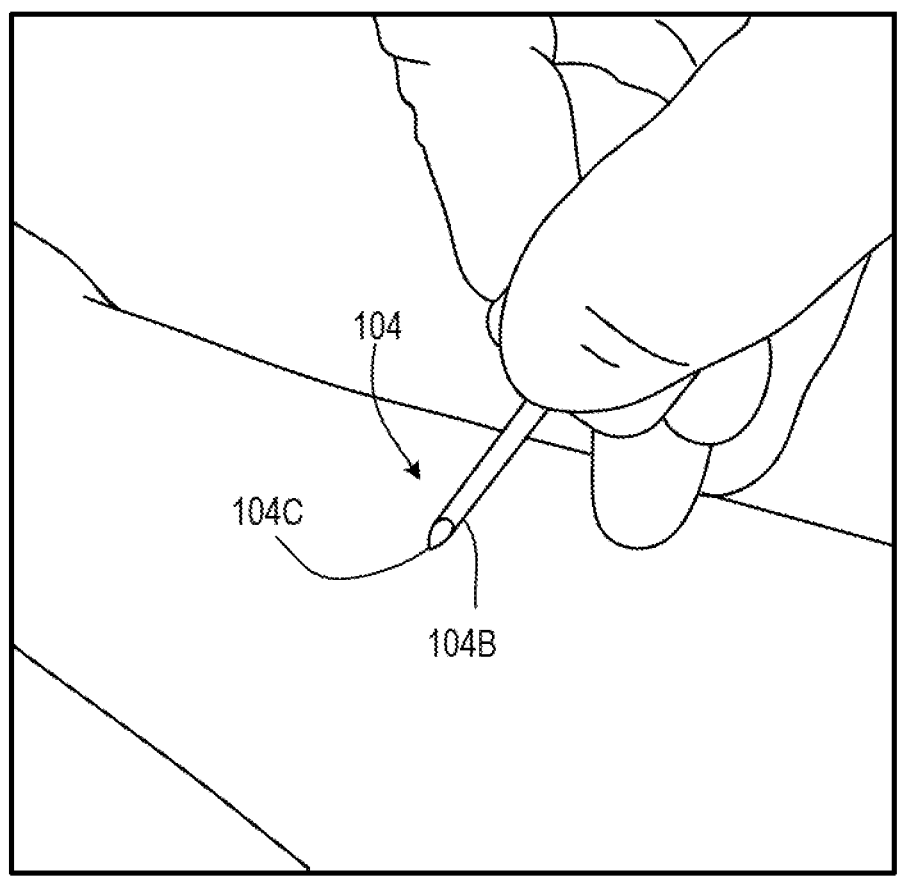
FIG. 2B is an illustration showing the user engaging scab tissue with the buttonhole tool.

Turning to FIG. 2B, the user may grasp the gripping portion 102 between his/her thumb and forefinger, with the ball of the thumb being placed in the indentation area on the front surface 103A and the forefinger being placed against back surface 103B. While gripping the tool 100, the user may place the first end portion 104B of prying portion 104 into contact with scab tissue. While holding gripping portion 102, the user makes contact with the scab tissue by placing scoop bevel 104C under the scab tissue. The user can then use the tool 100 to remove the scab tissue.

Figure 3A:
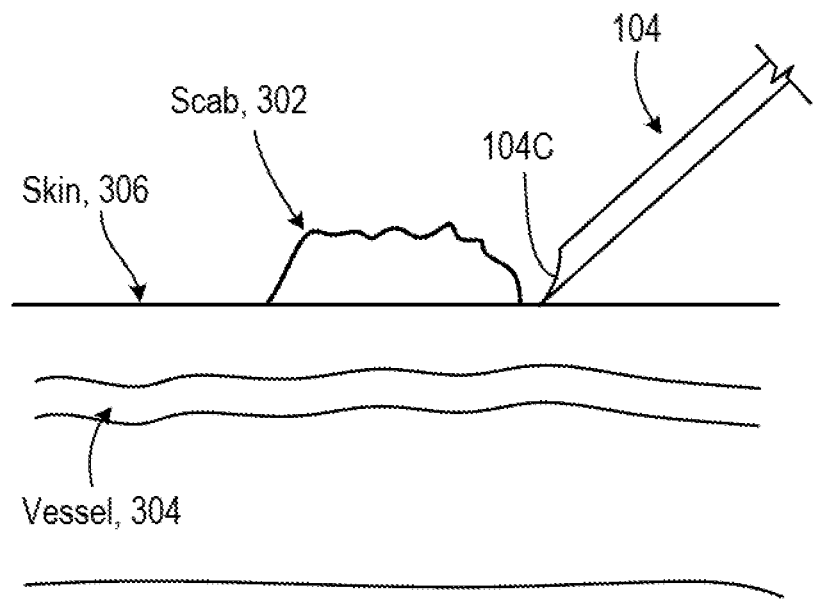
FIG. 3A-3D illustrate the use of the buttonhole tool during a buttonhole formation process.

FIGS. 3A to 3D illustrate the use of the buttonhole tool 100 during a buttonhole formation process. Referring to FIG. 3A, scab tissue 302 sits over skin 306 on top of a blood vessel 304. As noted, scab tissue 302 is developed over skin 306 at the location of vascular access portion based on earlier access(es) to the blood vessel during, for example, dialysis procedures. Here, the user may use buttonhole tool 100 to obtain subsequent vascular access with improved efficiency and safety, compared to using a simple dulled needle. Holding gripping portion 102 of a buttonhole tool 100 with a thumb and forefinger, the user can point prying portion 104 towards an edge of scab tissue 302. In particular, the user may point the prying portion 104 towards a bottom edge of scab tissue 302 bordering on the skin. Using scoop bevel 104C, the user may make contact on the subject's skin around the edge of the scab tissue. In the example above, the contact may be made by landing scoop bevel 104C around the edge of scab tissue 302.

Figure 3B:
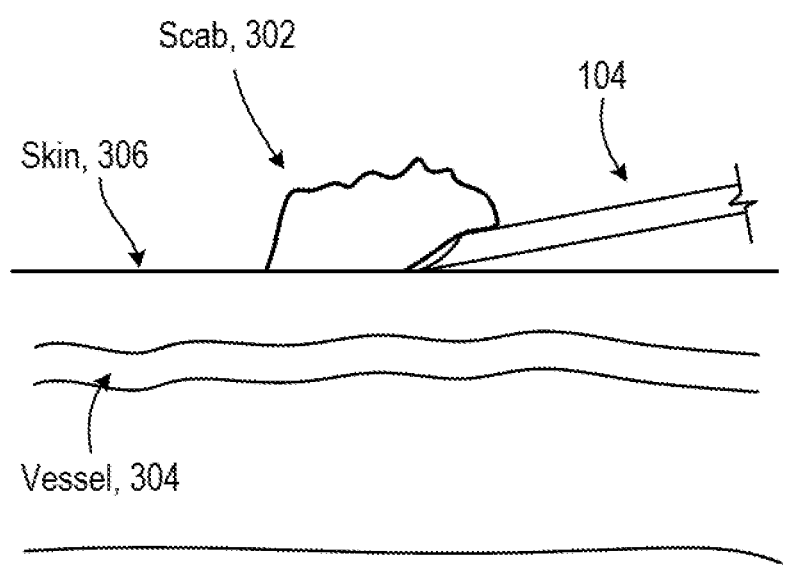

Turning to FIG. 3B, the user may utilize the elongated profile and scoop shape of scoop bevel 104C to get under scab tissue 302. Once the user has made some progress probing under scab tissue, the user may use the contact point where scoop bevel 104C touches the skin as a leverage point. Here, the user can apply a lifting force at gripping portion 102. Through the leverage point, the lifting force can generate a torque to lift at least a portion of scab tissue 302. The concave profile and the spoon shape make scoop bevel 104C particularly fit in breaking off scab tissue 302. Once scab tissue 302 is lifted a little, the user may push scoop bevel 104C of prying portion 104 further underneath scab tissue 302. From the new position, scoop bevel 104C is in contact with a larger volume of scab tissue 302 and is in position to further break scab tissue 302 off the skin. By pushing and lifting, a user can cause scab tissue 302 to break off skin 306 more efficiently and safely.

Figure 3C:
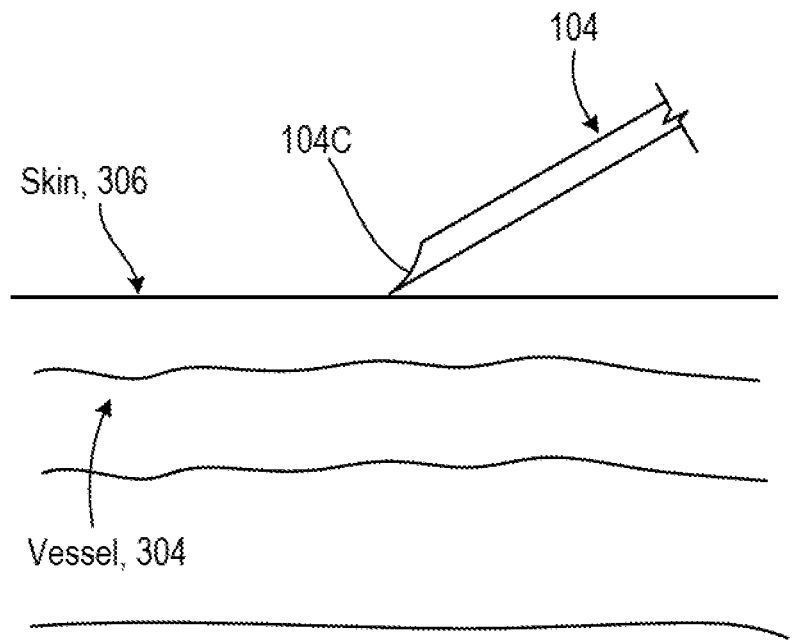
Figure 3D:
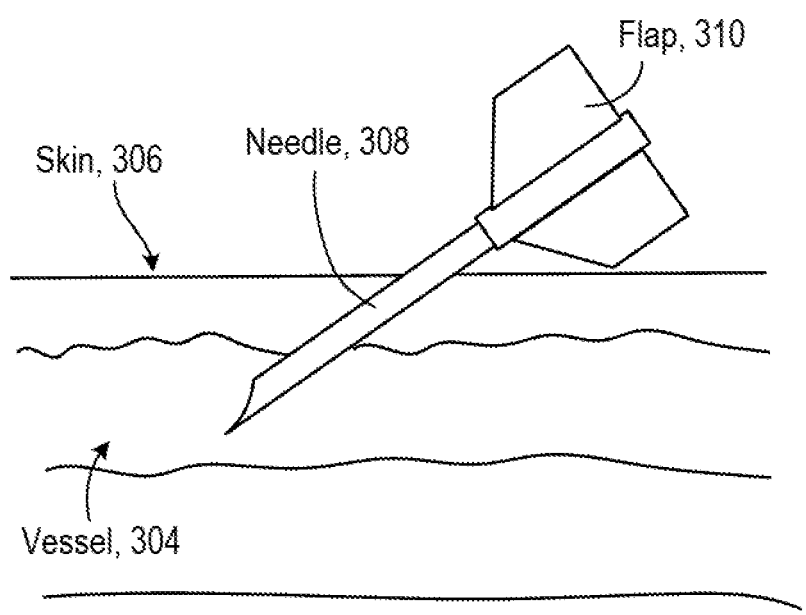

As illustrated in FIG. 3C, once scab tissue 302 is removed, skin 306 on top of blood vessel 304 is revealed. This exposes the area of the skin being used for vascular access. The user may obtain vascular access to the blood vessel by inserting a needle 308 through the skin 306 and into the blood vessel 304, as illustrated in FIG. 3D. The blood vessel may be part of the fistula, and can include a vein or an artery. The needle used may be, for example, a sharp needle. Once the process is repeated a number of times, a relatively permanent tunnel may be formed through the patient's skin where the scab tissue 302 was located. Once the tunnel is formed, a blunt needle may be used. In either event, the needle 308 includes a flap 310 on the distal end that can be taped to the patient's skin to provide fixation. The distal end may be coupled to tubing running into a dialysis machine and configured for infusion applications.

A number of implementations have been described. Nevertheless, it will be understood that various modifications may be made. For example, the gripping portion 102 includes front surface 103A that is substantially square, but other shapes may be employed. Examples may include a rectangular shape, an oval shape, a round shape, a diamond shape, a hexagonal shape, a pentagon shape, a trapezoid shape, or any appropriate polygon shape.

Accordingly, other implementations are within the scope of the following claims.

What is claimed is:

1. A tool comprising:
   a gripping portion comprising a first substantially flat base surface having a shape entirely bounded by at least three line segments and a second substantially flat base surface having the same shape and entirely bounded by at least three corresponding line segments, wherein:
      the second substantially flat base surface is arranged substantially parallel to the first substantially flat base surface and coupled to the first substantially flat base surface by multiple non-base substantially flat side surfaces, each of the multiple non-base substantially flat side surfaces directly connecting one of the three line segments of the first substantially flat base surface to the corresponding one of the three line segments of the second substantially flat base surface, and
      the gripping portion is shaped and sized such that a user can hold the gripping portion by pinching the first substantially flat base surface and the second substantially flat base surface between a thumb and a forefinger of the user; and
   a prying portion comprising a first end portion and a second portion comprising a shaft portion, the prying portion configured to have a longitudinal axis through the first end portion and the second end portion, the prying portion and the gripping portion formed from an identical material, wherein:
      the first end portion includes a tip with a pointed edge and has a concave profile from the tip to a proximal point of the first end portion,
      the first end portion is sized such that the user can hold the gripping portion to pry scab tissue away from a patient's skin,
      the shaft portion is directly connected to the gripping portion at one of the multiple non-base substantially flat side surfaces, and
      a diameter of the shaft portion is less than one third of a width of the shape of the first and second substantially flat base surfaces such that the longitudinal axis extends to split the first and second substantially flat base surfaces into substantially equal halves laterally on both sides of the longitudinal axis.

2. The tool of claim 1 wherein the first end portion of the prying portion includes a scoop bevel configured to pry scab tissue from a patient's skin.

3. The tool of claim 1 wherein the gripping portion and the prying portion are integrally formed.

4. The tool of claim 3 wherein the shaft portion is integrally coupled to the gripping portion at one of the multiple non-base substantially flat side surfaces.

5. The tool of claim 1 wherein the shaft portion is removably coupled to the gripping portion at one of the multiple non-base substantially flat side surfaces.

6. The tool of claim 1 wherein a length of the prying portion from the first end portion to the second end portion is between 1 cm to 8 cm.

7. The tool of claim 1 wherein the first substantially flat base surface and the second substantially flat base surface are generally rectangular and the multiple non-base substantially flat side surfaces include at least four side surfaces.

8. The tool of claim 7 wherein the first substantially flat base surface and the second substantially flat base surface are generally square.

9. The tool of claim 7 wherein the first substantially flat base surface and the second substantially flat base surface include rounded corners.

10. The tool of claim 7 wherein the first substantially flat base surface includes an indentation located substantially in the center of the first substantially flat base surface.

11. The tool of claim 10 wherein the indentation is a circular indentation.

12. The tool of claim 1 wherein the tool is packaged in a sterile package.

* * * * *